United States Patent [19]

Miller

[11] Patent Number: 5,429,058
[45] Date of Patent: Jul. 4, 1995

[54] HEART/LUNG MACHINE BASE

[76] Inventor: Mark F. Miller, 529 Regenhard Ave., Moorestown, N.J. 08057

[21] Appl. No.: 28,544

[22] Filed: Mar. 8, 1993

[51] Int. Cl.$^6$ ............................................. A47B 35/00
[52] U.S. Cl. ...................................... 108/50; 108/96; 108/32
[58] Field of Search ............... 604/4; 108/50, 91, 96, 108/106, 147, 90, 20-37, 93, 92

[56] References Cited

U.S. PATENT DOCUMENTS

| | | | |
|---|---|---|---|
| D. 90,710 | 9/1933 | Goodman | 108/92 X |
| 591,574 | 10/1897 | Smith | 108/32 X |
| 1,331,621 | 2/1920 | Carlin | 108/149 X |
| 1,699,710 | 1/1929 | Pearlman | 108/96 X |
| 1,881,475 | 10/1932 | Gibson | 108/106 |
| 2,575,725 | 11/1951 | McKay | 108/96 X |
| 2,935,205 | 5/1960 | Higgin | 108/91 X |
| 4,108,084 | 8/1978 | Fink | 108/149 X |
| 4,313,112 | 1/1982 | Foster | 108/92 X |
| 4,440,096 | 4/1984 | Rice et al. | 108/147 X |

FOREIGN PATENT DOCUMENTS

| | | | |
|---|---|---|---|
| 1196750 | 11/1959 | France | 108/30 |
| 1300853 | 7/1962 | France | 108/92 |
| 520617 | 4/1940 | United Kingdom | 108/91 |

OTHER PUBLICATIONS

Sarns MDX System Brochure (three pages).

*Primary Examiner*—Jose V. Chen
*Attorney, Agent, or Firm*—Ken Muncy

[57] ABSTRACT

A heart/lung machine base reduces tubing length by reducing the distance between the arterial pump and the surgical table. This is accomplished by providing a lift which will raise and lower the base in order to follow the movement of the surgical table. In this manner, slack in the tubing is unnecessary. Also, the cardioplegia pump can be positioned on an upper shelf in a relatively close position to the oxygenator. Tubing to the cardioplegia pump can therefore be reduced. To further minimize tubing length, the disposables can be configured in a generally straight line between the arterial pump and the patient. In order to maintain access and visibility of the vent and sucker pumps which are located beneath the cardioplegia shelf, an incline platform is provided. The arterial pump is positioned outwardly of uprights of the base such that its access and visibility is unhindered. Because of a mirror-image configuration for the base, it can readily be used in either a right-sided or left-sided configuration. An intruder discouraging device can be provided to protect the fragile components of the heart/lung machine from damage by personnel at the surgical field. In this manner, the heart/lung machine can be positioned relatively close to the surgical table in order to reduce tubing length.

23 Claims, 4 Drawing Sheets

FIG. 4

HEART/LUNG MACHINE BASE

BACKGROUND OF THE INVENTION

1. Field of the Invention

The present invention relates to a heart/lung machine base for a heart/lung machine.

2. Description of the Background Art

Various bases are known upon which heart/lung machines are positioned. These heart/lung machines are used during open heart surgery and other procedures to replace the function of the heart and lungs. A surgeon will insert tubes into the heart and blood vessels so that the patient's blood can be drained to the heart/lung machine, processed and pumped back into the patient.

Sterilized disposables such as tubing, filters, reservoirs and oxygenators are mounted onto the heart/lung machine. These disposables are used for one procedure and then discarded. The heart/lung machine is also composed of reusable hardware which does not come into contact with the patient's blood. Such modular hardware is mounted on a special cart or "base".

Conventional machines are configured in any number of ways but these configurations are often limited by the base upon which the machines are mounted. Currently, a heart/lung machine includes at least an arterial pump, a ventricular vent pump, a cardiotomy sucker pump, a cardioplegia delivery pump and other components.

Each of the pumps will propel blood or other substances to or from the patient. The machine sets close to the patient during surgery so that the tubing length can be as short as possible. There are several medical advantages to having short tubing length, most of which involve blood conservation.

Present heart/lung machine bases, however, impose limitations upon how short the tubing can be. Current machines make it necessary for the blood to travel a circuitous route from the patient, through the disposable components and back to the patient. The reasons for these limitations involve the fact that the heart/lung machines are designed to satisfy many requirements other than tubing length. Among these requirements are visibility (the ability of the operator to see all of the components), access (the ability of the operator to reach all the components) and protection of the fragile components from accidental breakage by personnel standing at the surgical table.

Due to these other criteria, existing heart/lung machine bases often sacrifice shorter tubing length for improved access and fragile component protection. Also, with such conventional heart/lung machine bases, assembly of the components of the heart/lung machine before each surgical operation can be difficult.

In other words, while there may be access to the components during operation of the pump, it can be awkward to assemble the circuit for heart/lung machines on conventional bases.

Also, in prior art heart/lung machine bases, the machine is vertically stationary during use thereby increasing tubing length in order to accommodate raising and lowering of the operating table upon which the patient is located. Also, because these bases are stationary in use, an operator is required to clamp the tubing when decreased venous drainage is desired.

Accordingly, a need in the art exists for a simple and effective heart/lung machine base which provides for short tubing length, visibility of components, easy access and protection of fragile components.

SUMMARY OF THE INVENTION

Accordingly, it is the primary object of the present invention to provide a heart/lung machine base which enables tubing length to be shortened.

Another object of the present invention is to provide a heart/lung machine base which provides for visibility of the machine components.

A further object of the present invention is to provide a heart/lung machine base which provides for ready access to the machine components both during assembly and operation of the heart/lung machine and enables the operator to configure the machine in several different arrangements.

Yet another object of the present invention is to provide a heart/lung machine base which can readily elevate and lower the heart/lung machine.

It is yet another object of the present invention to provide a heart/lung machine base which will provide for protection of the fragile components of the machine.

A further object of the present invention is to provide a heart/lung machine base which can be assembled in a right-sided or left-sided configuration.

Yet another object of the invention is to provide a heart/lung machine base which can be used with existing hardware and disposable components.

Another object of the present invention is to provide a heart/lung machine base which provides ready storage space for the user.

It is a further object of the present invention to provide a heart/lung machine base which is stable, durable, light-weight and portable.

A further object of the present invention is to provide a heart/lung machine base which requires limited maintenance, which is easy to manufacture and which is safe and reliable.

These and other objects of the present invention are fulfilled by providing a heart/lung machine base for a heart/lung machine having a plurality of pumps. This base has an upper and lower shelf with uprights extending therebetween. The components of the heart/lung machine are positioned on these shelves and uprights. On the lower shelf, a detachable inclined holding means can be provided. This inclined holding means will position pumps beneath the upper shelf at an angle so that they are readily visible. At least one intruder discouraging device can be mounted on one of the uprights to surround any of the disposables which extend outwardly of the base. This intruder discouraging device will protect fragile disposable components of the heart/lung machine.

The base can be divided between an upper portion and a support frame. Means are provided to elevate the upper portion relative to the support frame. Therefore, the uprights and shelves with the various pumps can be elevated as desired. Because of the use of an upper shelf, the cardioplegia pump can be positioned close to an in-line position between the patient and the arterial pump. This is just one feature decreasing tubing length in the present invention.

Further scope of applicability of the present invention will become apparent from the detailed description given hereinafter; however, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Figure 1:
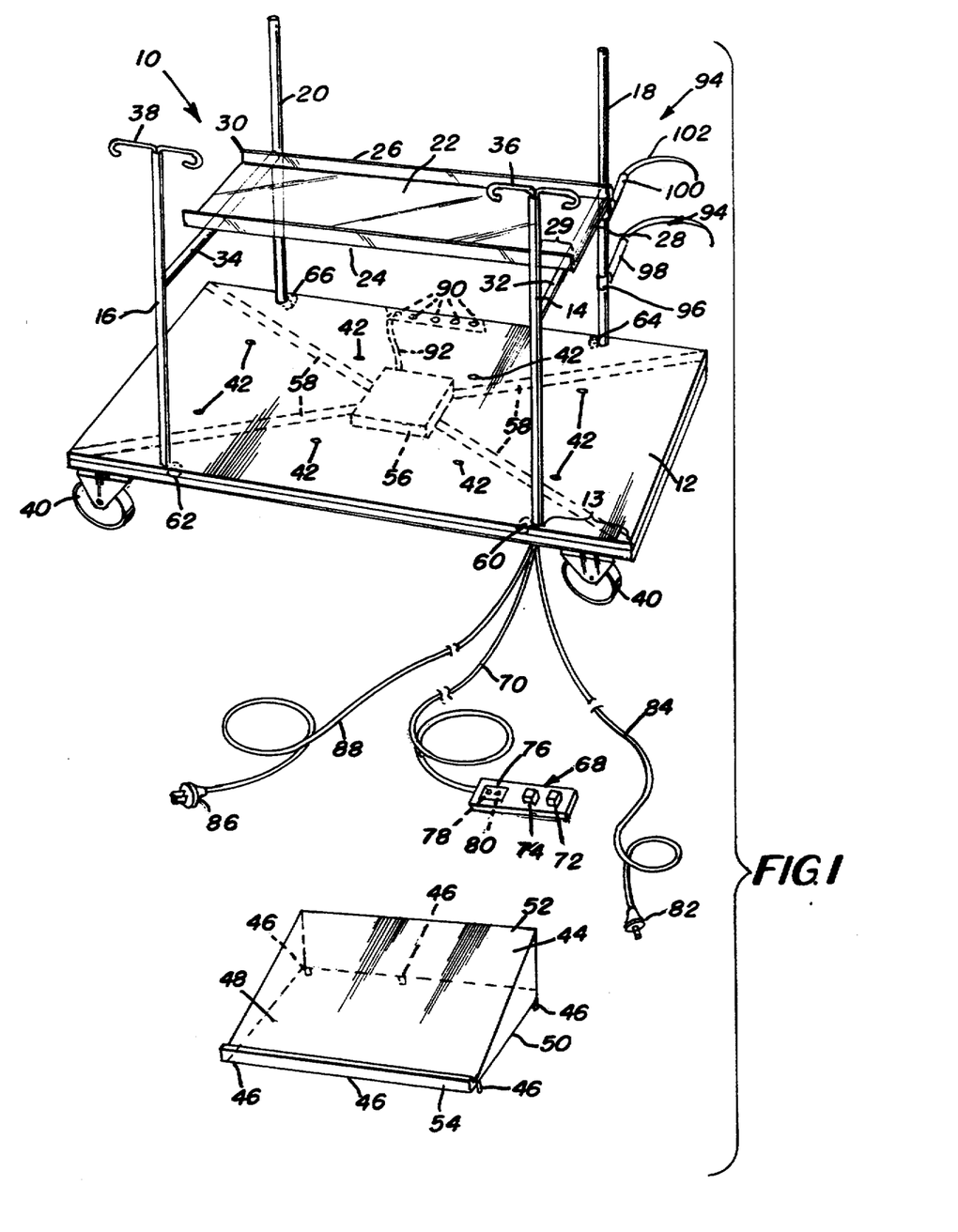
FIG. 1 is an exploded, perspective view of the heart/lung machine base of the present invention without any hardware or disposable of the heart/lung machine being positioned thereon.

Referring in detail to the drawings and with particular reference to FIG. 1, a heart/lung machine base 10 of the present invention is shown. The hardware and disposables of the heart/lung machine are not shown in FIGS. 1 and 2. The base 10 includes a lower shelf 12 and an upper shelf 22. The cardioplegia pump is normally positioned on this upper shelf 22 as will be discussed below. It should be recognized that any particular pump discussed as being in any particular location in the instant invention can readily be changed to another location, another pump or simply omitted as desired by the operator of the heart/lung machine.

Between the upper shelf 22 and lower shelf 12 are uprights. A front right upright 14, a front left upright 16, a rear right upright 18 and a rear left upright 20 are provided.

The upper shelf 22 has a front lip 24 and a rear lip 26. This will aid in preventing the cardioplegia pump or other pump from falling from the shelf. The upper shelf 22 has a right overhang 28 and a left overhang 30. The overhang extends beyond the uprights for a first distance 29 on each side of the base. A right support bar 32 and left support bar 34 are provided for fixing the upper shelf 22 to the respective uprights.

The upper shelf 22 can be detachable from the right support bar 32 and left support bar 34 if so desired. Therefore, if a cardioplegia pump is not used, this shelf can simply be moved to an out-of-the-way position. It is contemplated, however, that this shelf 22 will normally be permanently affixed to the support bars 32, 34.

The front uprights 14 and 16 have hooks 36 and 38 attached thereto. Blood, saline solution or any required equipment can be hung from these hooks 36, 38. If so desired, the rear uprights 18 and 20 can also be provided with such hooks. It is contemplated that these hooks 36, 38 shown in FIG. 1 can be detachably mounted on the uprights.

Beneath the lower shelf 12 are wheels 40. These wheels 40 are mounted towards the outermost corners of the lower shelf in order to provide a stable base. These wheels 40 enable easy transport of the heart/lung machine base 10.

On the upper surface of the lower shelf 12, mating holes 42 are provided. While eight mating holes are shown, any configuration and number of the mating holes 42 can be used. These mating holes 42 will receive detents 46 provided on the bottom of the inclined holding means 44. This inclined holding means or platform 44 is detachably mountable on the lower shelf 12. The detents 46 and mating holes 42 will prevent the platform 44 from undesirably moving.

The platform 44 has an inclined surface 48 which can receive pumps as will be discussed below. The bottom 50 of the platform is generally flat and will rest on the surface of the lower shelf 12. The rear 52 of the platform 44 is shown as being solid; however, this platform can have an opening for storage if so desired. Alternatively, the inclined surface 48 of the platform can be pivotable so that the interior of the platform 44 can act as a storage container. At the forward end of the platform 44 is a lip 54. This lip 54 will prevent the pumps resting on platform 44 from sliding from the platform.

Figure 2:
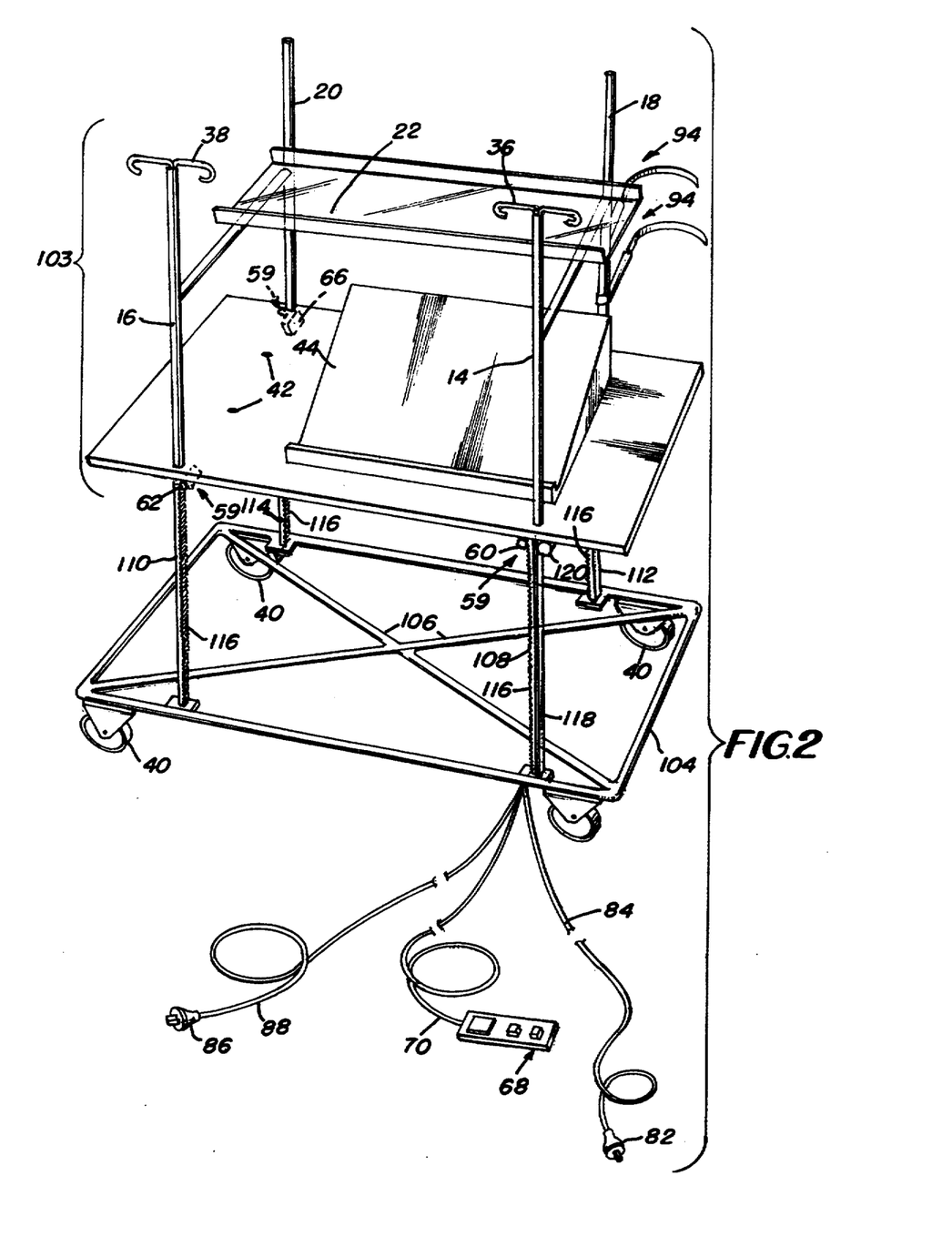
FIG. 2 is a perspective view of the heart/lung machine base of the present invention with the upper portion of the base in an elevated position.

As can be seen in FIG. 1, six detents are provided on the lower side of the platform 44. Therefore, two of the eight mating holes 42 provided in the lower shelf 12 will be exposed when the platform 44 is resting on the lower shelf. As seen in FIG. 2, the platform 44 can be positioned on the right-hand side of the lower shelf 12. Alternatively, the platform can be shifted such that it is positioned on the left-hand side of the platform. The exposed mating holes 42 in FIG. 2 would then be covered and the rightmost mating holes 42 would then be exposed. Due to this shiftability of platform 44 the heart/lung machine positioned on the base 10 can be set up for either a right-sided or left-sided configuration. This feature enables the heart/lung machine base to be optimally positioned for specific operating room designs.

As schematically shown in FIG. 1, a means for elevating is provided. This means for elevating includes a controller 56 positioned beneath the lower shelf 12. This controller 56 has connections 58 to various driving means 59. The driving means 59 include a right, front gear/motor 60, a left, front gear/motor 62, a right, rear gear/motor 64, and a left, rear gear/motor 66.

Operatively connected to the controller 56 by connection 70 is a control box 68. This control box 68 has two switches 72 and 74 which will cause the controller 56 to operate the driving means 59 to raise and lower the base as will be discussed below. While two switches are shown, it should be appreciated that a single toggle, type switch or any other suitable means can be used for activating the controller 56.

A cover 76 is provided on the controller 56. This cover 76 is over an on/off switch 78 for the base as well as an auto/manual switch 80 for the base. The cover 76 will prevent accidental operation of the switches 78, 80.

The cover 76 can be moved to an out-of-the-way position and the base then turned on or off by operation of switch 78. The operator can also select whether the base will operate in an automatic or manual mode by operating switch 80. The cover 76 can then be closed to prevent accidental operation of the switches 78, 80. The operator can then use his or her foot to operate the switches 72,74 to raise or lower the base.

Operation of the switch 80 will control which mode the base operates in. In the manual mode, the base is raised and lowered by operation of the switches 72, 74.

In the automatic mode, the base will automatically raise and lower upon raising or lowering of the operating table 140 on which the patient is located. The switches 72, 74 can be used to override this automatic operation. To carry out this automatic operation, the connector 82 is plugged into the operating table 140 as seen, for example, in FIG. 3. When the table controls 142 are operated to raise and lower the operating table 140, the controller 56 through wire 84 and connector 82 will then receive the signal to simultaneously raise or lower the table. If so desired, a time lag can be provided between operation of the table 140 and base 10. If such automatic operation is not desired, the switch 82 can be moved to the manual position. Of course, this automatic feature with switch 80, wire 84 and connector 82 can be omitted as so desired and the base will only be manually operated.

Apart from providing a foot operated control box 68, the switches for raising and lowering the base could be mounted on any of the uprights 14, 16, 18, 20 or on the upper or lower shelf. It is merely desired that the controls for raising and lowering the heart/lung machine base 10 be conveniently located for an operator and be in a position where accidental operation thereof can be avoided. If so desired, a cover can be provided over any of these switches such that accidental operation is assuredly prevented.

When assembling conventional heart/lung machines, the operator is often required to be in an awkward position. The operator must bend over in order to assemble the tubing and other components of the heart/lung machine. Over time, this can be uncomfortable for the operator.

With the raisable base of the instant invention, the heart/lung machine base 10 can be elevated such that the operator has easy access to the areas of the base. The hardware and disposable components of the heart/lung machine can then be easily assembled. The machine can then be lowered to a normal use position.

Apart from aiding assembly of the heart/lung machine, the adjustability of the base 10 also enables the heart/lung machine to follow the up and down movement of the patient on table 140. In conventional machines, excessive tubing length is required because the heart/lung machine is normally nonmovable during use. Therefore to accommodate vertical movement of the patient and table, slack must be provided in the tubing. To avoid such unneeded slack, the instant base 10 can be vertically adjusted in order to follow the movements of the patient.

Apart from reducing tubing length, this height adjustment feature for the base 10 can also have a direct impact on the perfusion process. For example, when decreased venous drainage is desired, the base with the reservoir mounted thereon can be raised relative to the patient. Conventionally to decrease venous drainage, the tubing leading to the reservoir is partially clamped. By simply maneuvering the base 10 to the desired height, a reduced flow to the reservoir can be had with the instant base. Of course, this base can also be operated to increase flow as so desired. Thus, the height adjustment feature of the base 10 of the present invention can aid in the operation of the heart/lung machine.

The control box 68 and table lift connector 82 form an operating means. This control box 68 and table connector 82 are connected to the controller 56 by wires 70 and 84. An additional wire 88 is provided between a plug 86 and the controller 56. This plug 86 will merely supply electric power to the base 10. It is possible, of course, to omit this plug and use a battery to power the heart/lung machine base.

On the rear side of the base 10 are a plurality of outlets 90. These outlets 90 are connected to the controller 56 through a connection 92. When power is supplied to the controller 56 via the plug 86 or optional batteries, power is then also supplied to the outlets 90. The various equipment used on the base 10 can be plugged into these outlets 90 if so desired. This can reduce the clutter of electric cords used in the area of the heart/lung machine. Of course, these outlets 90 can be omitted if so desired.

On the rear right upright 18 are two intruder discouraging devices 94. While two devices are shown in the figures, it should be appreciated that any number of devices can be used. A connection 96 is provided for detachably affixing these devices 94 to the upright 18.

Figure 3:
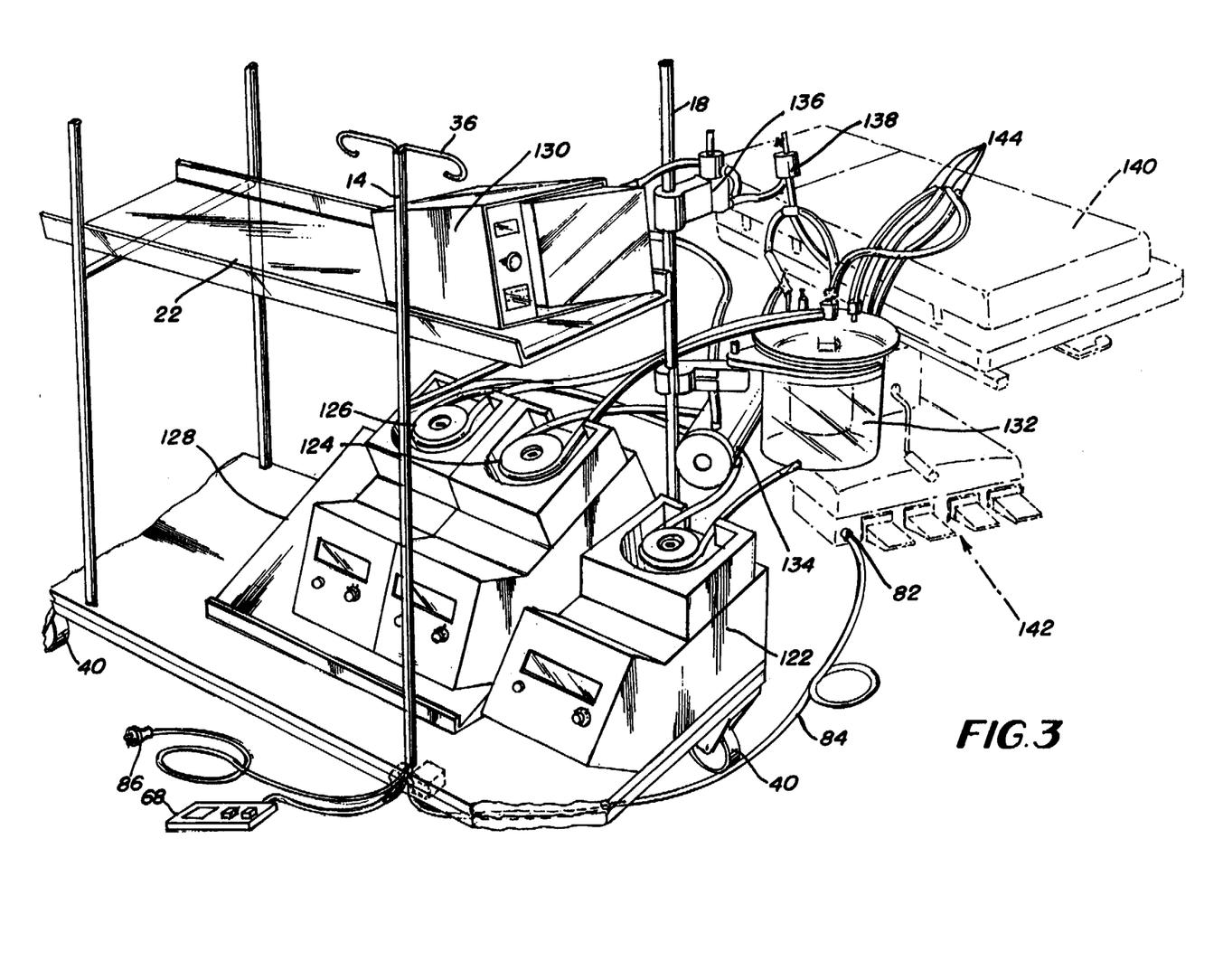
FIG. 3 is a perspective view of the heart/lung machine base of the present invention with the hardware and disposable components mounted thereon.
Figure 4:
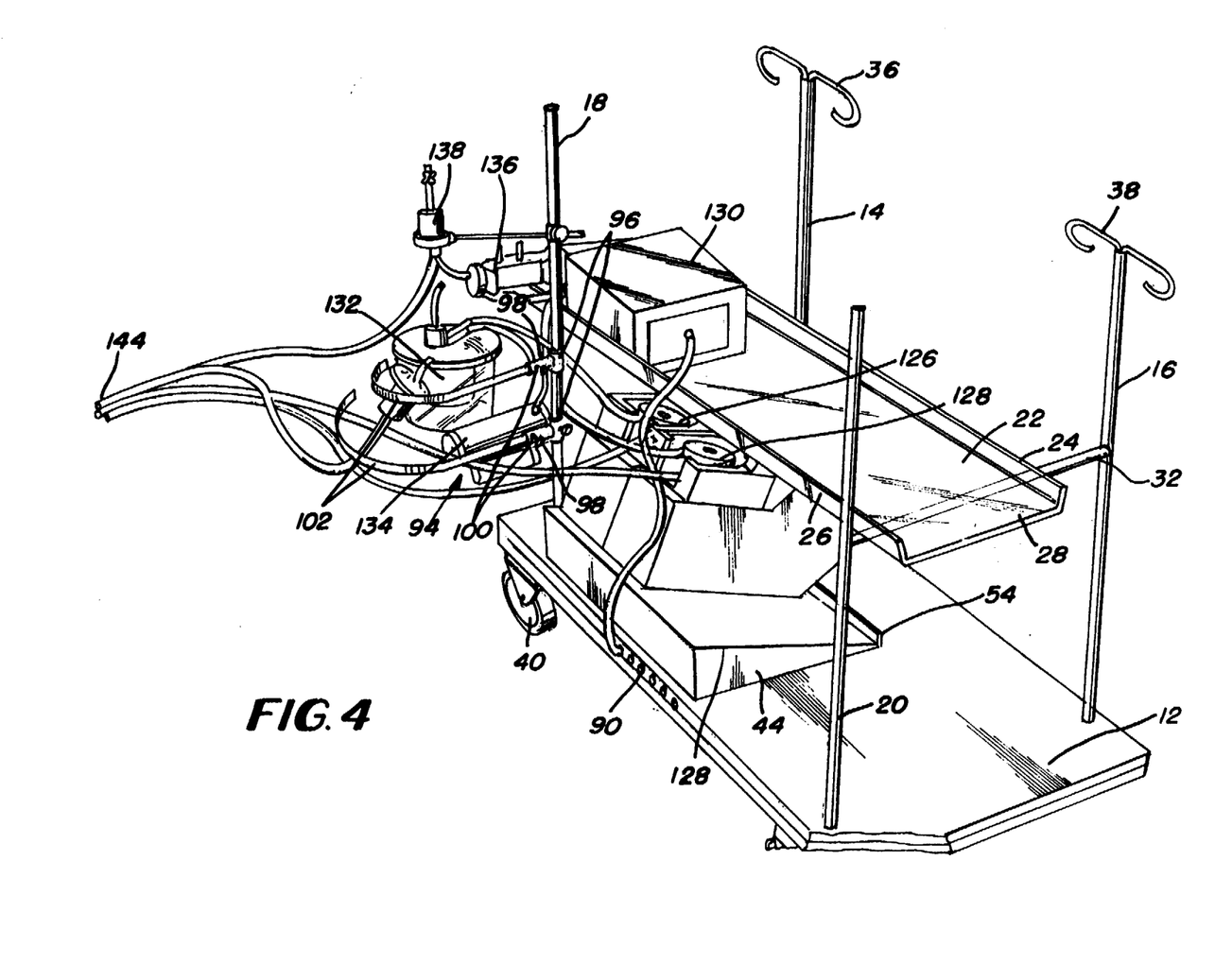
FIG. 4 is a rear perspective view of the heart/lung machine base of the present invention with the hardware and disposable components of the heart/lung machine mounted thereon.

The intruder discouraging devices 94 include a first section 98 and a second section 102. These sections 98 and 102 are connected at a pivot 100. Therefore, the positioning of the intruder discouraging device 94 can be readily adjusted. This intruder discouraging device will protect the disposables and especially the disposables which overhang the base 10 as seen in FIGS. 3 and 4.

Therefore, the disposables can be positioned relatively close to the surgical table in order to reduce tubing length. The problem of inadvertent breakage of fragile disposables by personnel standing at the table is avoided through the use of these intruder discouraging devices 94. Conventionally, the solution to such a problem has been to increase the tubing length in order to move the fragile components further from the surgical table 140. By using these intruder discouraging devices 94, a physical barrier is interposed between the disposables and the personnel at the table. The intruder discouraging devices 94, however, will not block access to or the view of the disposables.

While pivoting two section intruder discouraging devices 94 have been shown, it should be appreciated that any suitable intruder discouraging device can be provided. For example, a rigid, one-piece structure can be used which is permanently or temporarily mounted to one or both of the rear uprights. Moreover, a separate upright (not shown) can also be provided adjacent either the right and/or left rear sides of the base 10 for receiving these intruder discouraging devices 94. In that manner, these devices do not necessarily have to be mounted on the rear uprights 18 or 20.

While FIG. 1 indicates the intruder discouraging devices 94 as being attached to the rear right upright 18, these devices can merely be flipped over and attached to the rear left upright 20. This therefore, enables use of the device by either a right-side or left-sided pump set up. The movability of the platform 44 between the left and right sides also aids right or left-handed use. It should be recognized that the intruder discouraging devices 94 as well as the platform 44 can be omitted from the base 10 if so desired.

As seen in FIG. 2, the base 10 is provided with an upper portion 103 and a lower support frame 104. The support frame 104 includes crossbars 106 which can be omitted if so desired. The uprights 14, 16, 18 and 20 of the instant invention are hollow with inner uprights 108, 110, 112, 114 being provided therein, respectively. On inner surfaces of these inner uprights 108, 110, 112 and 114 are racks 116. These racks 116 will mate with the gears/motors 60, 62, 64 and 66. These gears/motors 60, 62, 64, 66 are connected to the controller 56. The gears and racks form a rack and pinion arrangement whereby the upper portion of the base 106 can be raised and lowered relative to the support frame 104.

Extending through one of the uprights is a channel guide 118 for receiving the wires 70, 84 and 88. A connector guide 120 is provided at the lower surface of the lower shelf 12. It is contemplated that the controller 56 can have an extension retraction means such that a variable length of wire can be fed from the controller 56 through the connector guide 120 and the channel guide 118. In this manner, the length of wire 70, 84, 88 extending from the support frame will remain consistent while the length of wire between the controller 56 and support frame 104 can vary as the upper portion 103 of the base is raised and lowered. In other words, as the upper portion 103 of the base moves upwardly, wire will be pulled from the controller 56. On the other hand, when the upper portion 103 is lowered the wire will be retracted into the controller 56.

Of course, any suitable arrangement for the wires 70, 84, 88 can be had. The wires 70, 84 and 88 can be connected directly to the controller without the use of a connector guide 120 and channel guide 118. A sufficient length of wire would be provided such that the wires would hang from the controller 56 without adversely effecting the positioning of the control box 68, connector 82 and plug 86 during raising and lowering of the shelves 12, 22 and uprights 14, 16, 18 and 20. Many other arrangements for the connection of the control box 68, connector 82 and plug 86 are contemplated. For example, the hardware connection can be omitted and a radio control arrangement can be used for control box 68 and the optional connector 82. Other arrangements are equally applicable for connecting these elements.

In FIG. 2, the upper portion is shown as being separate from the support frame 104. Because the wheels 40 are positioned towards the edges of the base to provide stability, the support frame 104 is necessary. It is possible, however, that the wheels 40 can be directly mounted to the bottom of the inner uprights 108, 110, 112 and 114. The support frame 104 would then be omitted.

Moreover, instead of using a rack and pinion driving arrangement, any suitable means can be used for raising and lowering the base. For example, a pulley and belt arrangement, a threaded screw and ball arrangement or any other known means can be used. Also, instead of providing a driving means 59 at each of the uprights, any number of driving means could be used. For example, only one driving means can be used on a selected one of the uprights. Alternatively, a central post could be provided for lifting the platform instead of the use of inner uprights and rack and pinion gears. The base 10 can be elevated by a hydraulic arrangement, centrally provided screw or any other suitable lifting design. It is merely necessary that the base be relatively stable when raised and lowered.

Turning now to FIGS. 3 and 4, the base 10 with the hardware and disposables mounted thereon are shown. The disposables include such things as tubing 144, venous reservoir 132, oxygenator 134 and cardioplegia bubble trap 138. The arterial pump 122, vent pump 124 sucker pump 126, cardioplegia pump 130 and heat exchanger 136 are reusable hardware elements of the heart/lung machine.

The arterial pump 122 is positioned on a ledge or overhang 28 of the lower shelf 12. As should be evident, this arterial pump can either be positioned on the right overhang 28 or the left overhang 30. Use of this overhang allows the hardware for mounting the disposables to be attached to either the uprights 18 or 20 in a way that does not obstruct the operators visibility or access to the disposables and hardware.

The ledge or overhang 28 also allows the disposables to be position close to an in-line position between the arterial pump 122 and the point of the surgical field where the tubing must go. Because the shortest distance between two points is a straight line, this configuration results in the shortest tubing length among possible configurations.

To further reduce tubing length, the intruder discouraging device 94 is provided as noted above. In this manner, the heart/lung machine can be positioned relatively close to the surgical table in order to reduce the required tubing length. The intruder discouraging device 94 will protect fragile disposables while allowing access and visibility by the operator.

In reducing tubing length, the oxygenator 134 is positioned almost exactly in the in-line position. The upper shelf 22 enables the cardioplegia pump 30 to be positioned relatively close to this in-line position and thereby also reduces tubing length. In particular, when blood cardioplegia is used, oxygenated blood goes from the oxygenator 134 via tubing 144 through the cardioplegia pump 130 and then through other disposables and back to the patient. To reduce this tubing length, it is best to position all of the above cardioplegia components as close to the theoretical line between the arterial pump 122 and the patient.

By use of the cardioplegia or upper shelf 22, the cardioplegia pump 130 can be placed relatively close to this theoretical line and much closer than that of conventional heart/lung machines. The cardioplegia pump 130 sets on the upper shelf 22 just above the oxygenator 134. Thus, the tubing length of the cardioplegia circuit is reduced. Of course, if a cardioplegia pump is not used, this pump and tubing can be omitted from the circuit. In maximizing tubing length reduction, the cardioplegia pump 130 rests on either the right or left overhang 28, 30. Tubing traveling to this pump 130 can then be positioned outwardly of either upright 18 or 20. Because the uprights are in an out of the way position, tubing length to the pump 130 need not be increased.

Use of the upper shelf 22 could hinder visibility of the pumps 124 and 126 positioned therebelow. To avoid this problem, the upper shelf 22 is transparent as shown in FIGS. 1 and 2. This shelf can be made from plexiglass, a wire mesh or any other suitable material. In that manner, visibility of the components of the heart/lung machine are not obstructed; however, the use of a transparent shelf aids visibility while preventing leakage of any fluids from the upper shelf onto the lower components of the heart/lung machine. Also, material such as plexiglass can be easily wiped down when cleaning the base 10.

As seen in the figures, the cardioplegia pump 130 extends generally across the entire width of the upper shelf 22. Of course, this shelf 22 can be increased in width if so desired in order to expand the area available. It is merely necessary that this shelf 22 does not block the pumps 124 and 126 below it. The use of a plexiglass shelf aids in the visibility of these pumps. Because the cardioplegia pump 130 does not extend along the full length of the upper shelf 22, a storage area is provided. This area on the upper shelf 22 can hold syringes, unused disposables, supplies, the pump record, etc.

While it has been noted that the plexiglass feature of shelf 22 aids in viewing the vent pump 124 and sucker pump 126, the platform 44 also aids this feature. Placement of the upper shelf 22 over the other pumps 124, 126 can create problems in reducing the visibility and access to these pumps on the lower shelf as noted. Apart from the use of the plexiglass or other see-through upper shelf 22, the triangle-shaped platform 44 acts as an inclined holding means for pumps 122 and 124. This platform 44 tilts these pumps so that the operator has visibility and access to the tubing therein. While only two pumps are shown on platform 44, extra space 128 has been provided such that additional pumps can be added on the platform 44 as so desired. Of course, this platform 44 can be omitted and the pumps placed directly on the lower shelf 12.

While the uprights 14, 16, 18 and 20 have been shown as vertical posts, it should be appreciated that an arch could be formed between these supports. For example, the two front uprights 14, 16 can be connected with an arch and the two rear uprights 18, 20 can also be connected by another arch. Alternatively, an arch or other support could be provided between the two side uprights. Any of these arrangements would merely add structural rigidity to the base of the instant invention.

It should be recognized that the particular hardware and disposables discussed are merely illustrative. Any desired heart/lung machine components and configuration can be used as desired. Moreover, any one of the intruder discouraging device 94, platform 44, means for elevating and/or upper shelf 22 can be omitted if so desired. Thus, great flexibility can be had when manufacturing the heart/lung machine base 10.

The heart/lung machine can be easily used by either a left or right-sided configuration as previously set forth. By providing the lift means of the instant invention, the base can be elevated to any desired height such that the operator can comfortably assemble the heart/lung machine. Also, drainage from the patient can be regulated by varying the height of the base 10 during its use. By raising and lowering the base, the tubing length required can also be reduced. Because it is possible to simultaneously raise or lower all the hardware and disposables mounted on the heart/lung machine base, shorter tubing length can be had between the patient and the heart/lung machine. In other words, the additional "slack" in the tubing which is required in conventional systems can be eliminated with the instant invention while raising and lowering of the patient on the surgical table 140 is not hindered.

The instant invention also reduces tubing length by enabling the arterial pump and oxygenator to be in an in-line position. The distance to the cardioplegia pump 130 can also be reduced when this pump is placed on the upper shelf 22. By using the upper shelf 22 with the platform 44, the visibility and access to the lower pumps 122, 124 are not hindered. Also, the intruder discouraging device 94 enables the base to be positioned relatively close to the surgical table 140 without danger to the fragile components of the heart/lung machine. This feature also aids in reducing the tubing length.

The heart/lung machine base of the instant invention can be used with existing disposables and hardware. The base is stable, durable, light weight and portable while requiring only limited maintenance. This base 10 provides a safe, reliable support for the heart/lung machine.

Of course, the described heart/lung machine base can be used in other forms of extracorporeal circulation, such as extracorporeal membrane oxygenation (ECMO), ventricular assists devices (VAD) or cardiopulmonary support (CPS).

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims. WHAT IS CLAIMED:

What is claimed:

1. A heart/lung machine base for a heart/lung machine having a plurality of pumps, the heart/lung machine base comprising:

a lower shelf and an upper shelf, each of the shelves having a left side and a right side, both of the shelves receiving at least one pump and both shelves being a permanent fixed distance from one another;

uprights connecting the upper and lower shelves, the uprights being positioned inwardly from the left and right sides of each of the shelves, the uprights being generally spaced a first distance from one side of the upper shelf and a second distance from the same side of the lower shelf, the second distance being greater than the first distance, at least one of the uprights extending above the upper shelf; and inclined holding means on the lower shelf for receiving the at least one pump on the lower shelf, the holding means positioning the at least one pump at an inclined position, the at least one pump received on the upper shelf being a cardioplegia pump and wherein a part of the cardioplegia pump is positioned outwardly of the uprights on the upper shelf.

2. The heart/lung machine base as recited in claim 1, wherein the holding means comprises a platform having an inclined surface and a lower surface, the lower surface of the platform being positionable on the lower shelf and the inclined surface of the platform receiving at least one pump.

3. The heart/lung machine base as recited in claim 2, wherein the lower surface of the platform has a plurality of detents provided thereon and wherein a plurality of mating holes are provided on the lower shelf into some of which the detents of the platform are inserted when the platform is on the lower shelf, the platform being detachably mounted on the lower shelf by the detents and at least some of the mating holes.

4. The heart/lung machine base as recited in claim 3, wherein the platform has a lip provided on a lower edge of the inclined surface, the lip aiding in holding the at least one pump on the platform and wherein the platform is readily detachably positioned on one of a right and a left side of the lower shelf.

5. The heart/lung machine base as recited in claim 1, further comprising at least one intruder discouraging device detachably mounted on one of the uprights.

6. The heart/lung machine base as recited in claim 5, wherein the heart/lung machine has disposables which are positioned outwardly of the base, the disposables include an oxygenator, the at least one intruder discouraging device partially surrounds the disposables positioned outwardly of the base to thereby protect the disposables.

7. The heart/lung machine base as recited in claim 6, wherein each of the intruder discouraging devices includes two pivotally joined sections, one of the sections being detachably mounted to the upright.

8. The heart/lung machine base as recited in claim 1, further comprising means for elevating the upper and lower shelves and the pumps positioned thereon.

9. The heart/lung machine base as recited in claim 8, wherein the base has an upper portion and a support frame, the upper and lower shelves being on the upper portion of the base, the uprights being hollow and being mounted on the upper portion of the base, inner uprights being mounted on the support frame and being positioned within the uprights on the upper portion of the base, the means for elevating moving the upper portion of the base relative to the support frame.

10. The heart/lung machine base as recited in claim 9, wherein the means for elevating comprises a controller operatively connected to driving means at least at one of the uprights and operating means operatively connected to the controller for causing upward and downward movement of the upper portion of the base.

11. The heart/lung machine base as recited in claim 10, wherein the driving means includes a rack and pinion gear for each of the uprights, the racks being mounted on each of the inner uprights and the gears being mounted beneath the upper portion of the base adjacent each of the inner uprights and in engagement with the racks.

12. The heart/lung machine base as recited in claim 1, wherein the at least one pump received on the lower shelf is at least an arterial pump, and wherein the arterial pump is positioned on the lower shelf outwardly of the uprights and beneath at least a part of the cardioplegia pump on the upper shelf.

13. The heart/lung machine base as recited in claim 12, wherein the first and second distances are provided on both right and left sides of the base such that the cardioplegia pump and the arterial pump are selectively positioned outwardly of the uprights on one of the right and left sides of the pump base.

14. The heart/lung machine base as recited in claim 1, wherein four uprights are provided and wherein each of the uprights extends above the upper shelf.

15. A heart/lung machine base for a heart/lung machine having at least one pump and disposables, the heart/lung machine base comprising:
    at least one shelf for receiving the at least one of pump, some of the disposables of the heart/lung machine being positioned outwardly of the shelf and being operatively connected to the at least one pump;
    at least one upright mounted on the at least one shelf; and
    an intruder discouraging device detachably mounted on the at least one upright, the intruder discouraging device partially surrounding in a horizontal plane a majority of the disposables extending outwardly of the shelf to thereby protect the disposables, the intruder discouraging device includes a plurality of pivotally joined sections, one of the sections being detachably mounted to the at least one upright.

16. The heart/lung machine base as recited in claim 15, wherein four uprights are provided and wherein a plurality of intruder discouraging devices are provided, all of the intruder discouraging devices being detachably mounted on a selected one of the uprights, at least some of the disposables also being detachably mounted on the selected one of the uprights.

17. The heart/lung machine base as recited in claim 16, wherein two shelves are provided as the at least one shelf, each of the shelves receiving at least one pump, one of the shelves being positioned over the other shelf and both shelves being connected to the uprights and extending beyond the uprights, the base further comprising inclined holding means on a lower one of the shelves for receiving one of the at least one pumps on the lower shelf, the holding means positioning the one of the at least one pump at an inclined position, the inclined holding means being detachably mounted on the shelf.

18. The heart/lung machine base as recited in claim 17, wherein the base has an upper portion and a support frame, the upper and lower shelves being on the upper portion of the base, the uprights being hollow and being mounted on the upper portion of the base, inner uprights being mounted on the support frame and being positioned within the uprights on the upper portion of the base, the base further comprising means for elevating the upper and lower shelves and the pumps positioned thereon, the means for elevating moving the upper portion of the base relative to the support frame, the means for elevating comprises a controller operatively connected to driving means at least at one of the uprights and operating means operatively connected to the controller for causing upward and downward movement of the upper portion of the base.

19. The heart/lung machine base as recited in claim 15, wherein the base has an upper portion and a support frame, the at least one shelf being on the upper portion of the base, the at least one upright being hollow and being mounted on the upper portion of the base, at least one inner upright being mounted on the support frame and being positioned within the at least one upright on the upper portion of the base, the base further comprising means for elevating the upper portion of the base relative to the support frame, the means for elevating comprises a controller operatively connected to driving means at least at the at least one upright and operating means operatively connected to the controller for causing upward and downward movement of the upper portion of the base.

20. The heart/lung machine base as recited in claim 19, wherein the driving means includes a rack and pinion gear for each of the uprights, the racks being mounted on each of the at least one inner upright and the gears being mounted beneath the upper portion of the base adjacent each of the at least one inner upright and in engagement with the racks.

21. A heart/lung machine base for a heart/lung machine having a plurality of pumps, the heart/lung machine base comprising:
    an upper portion of the base and a support frame;
    a lower shelf and an upper shelf, each of the shelves having a left side and a right side, both of the shelves receiving at least one pump and both shelves being a permanent fixed distance from one another, the upper and lower shelves being on the upper portion of the base;
    hollow uprights connecting the upper and lower shelves, the uprights being mounted on the upper portion of the base;

inner uprights mounted on the support frame, the inner uprights being positioned within the uprights on the upper portion of the base;

holding means on the lower shelf for receiving the at least one pump on the lower shelf; and means for elevating the upper and lower shelves and the pumps positioned thereon, the means for elevating moving the upper portion of the base relative to the support frame.

22. A heart/lung machine base for a heart/lung machine having a plurality of pumps, the heart/lung machine base comprising:

a lower shelf and an upper shelf, each of the shelves having a left side and a right side, both of the shelves receiving at least one pump and both shelves being a permanent fixed distance from one another;

uprights connecting the upper and lower shelves, the uprights being positioned inwardly from the left and right sides of each of the shelves, the uprights being generally spaced a first distance from one side of the upper shelf and a second distance from the same side of the lower shelf, the second distance being greater than the first distance;

inclined holding means on the lower shelf for receiving the at least one pump on the lower shelf, the holding means positioning the at least one pump at an inclined position, the holding means comprises a platform having an inclined surface and a lower surface, the lower surface of the platform being detachably positioned on the lower shelf; and a plurality of detents on the lower surface of the platform and a plurality of mating holes on the lower shelf, detents of the platform being inserted into some of the mating holes on the lower shelf when the platform is on the lower shelf, the platform being detachably mounted on the lower shelf by the detents and at least some of the mating holes.

23. The heart/lung machine base as recited in claim 22, wherein the platform has a lip provided on a lower edge of the inclined surface, the lip aiding in holding at least one pump on the platform and wherein the platform is readily positioned on one of a right and a left side of the lower shelf.

* * * * *